(12) United States Patent
Miller et al.

(10) Patent No.: US 6,402,720 B1
(45) Date of Patent: *Jun. 11, 2002

(54) BALLOON CATHETER WITH ELONGATED FLEXIBLE TIP

(75) Inventors: Jay Frederick Miller, Miramar; Edward J. Play, Weston; Nicholas Martino, Miami Lakes, all of FL (US)

(73) Assignee: Cordis Corporation, Miami Lakes, FL (US)

( * ) Notice: This patent issued on a continued prosecution application filed under 37 CFR 1.53(d), and is subject to the twenty year patent term provisions of 35 U.S.C. 154(a)(2).

Subject to any disclaimer, the term of this patent is extended or adjusted under 35 U.S.C. 154(b) by 0 days.

(21) Appl. No.: 08/995,781

(22) Filed: Dec. 22, 1997

(51) Int. Cl.$^7$ .............................................. A61M 29/00
(52) U.S. Cl. ................................................... 604/96.01
(58) Field of Search .......................... 604/52, 93, 96, 604/101, 103, 104, 164, 166, 264, 280, 282, 912, 914, 915, 919, 525; 600/433–435, 585; 264/310

(56) References Cited

U.S. PATENT DOCUMENTS

| | | | |
|---|---|---|---|
| 3,498,286 A | | 3/1970 | Polvani et al. |
| 3,833,003 A | * | 9/1974 | Taricco ..................... 604/96 |
| 4,385,635 A | | 5/1983 | Ruiz |
| 4,531,943 A | | 7/1985 | Van Tassel et al. |
| 4,563,181 A | * | 1/1986 | Wijayarathna et al. ...... 604/280 |
| 4,588,398 A | | 5/1986 | Daugherty et al. |
| 4,596,563 A | | 6/1986 | Pande |
| 4,636,346 A | | 1/1987 | Gold et al. |
| 4,641,654 A | * | 2/1987 | Samson et al. ............... 604/95 |
| 4,842,590 A | * | 6/1989 | Tanabe et al. ............... 604/282 |
| 4,850,969 A | * | 7/1989 | Jackson ...................... 604/102 |
| 4,904,431 A | * | 2/1990 | O'Maleki .................... 264/103 |
| 5,078,702 A | * | 1/1992 | Pomeranz .................... 604/280 |
| 5,156,785 A | * | 10/1992 | Zdrahala ..................... 604/264 |
| 5,254,090 A | * | 10/1993 | Lombardi et al. ............ 604/96 |
| 5,273,536 A | * | 12/1993 | Savas ......................... 604/96 |
| 5,312,356 A | * | 5/1994 | Engelson et al. ............ 604/265 |
| 5,318,032 A | * | 6/1994 | Lonsbury et al. ........... 604/282 |
| 5,425,712 A | | 6/1995 | Goodin |
| 5,453,099 A | * | 9/1995 | Lee et al. .................... 604/264 |
| 5,454,788 A | * | 10/1995 | Walker et al. ................ 604/96 |
| 5,489,264 A | * | 2/1996 | Salo .......................... 604/101 |
| 5,538,510 A | | 7/1996 | Fontirroche et al. |
| 5,542,926 A | * | 8/1996 | Crocker ....................... 604/96 |
| 5,542,937 A | * | 8/1996 | Chee et al. .................. 604/264 |
| 5,554,139 A | * | 9/1996 | Okajima ..................... 604/282 |
| 5,599,325 A | * | 2/1997 | Ju et al. ...................... 604/264 |
| 5,707,354 A | * | 1/1998 | Salmon et al. ............... 604/96 |
| 5,707,358 A | * | 1/1998 | Wright ........................ 604/96 |
| 5,795,341 A | * | 8/1998 | Samson ....................... 604/264 |
| 5,797,945 A | * | 8/1998 | Dunham ..................... 604/101 |
| 5,820,594 A | | 10/1998 | Fontirroche et al. |
| 5,824,173 A | | 10/1998 | Fontirroche et al. |
| 5,851,464 A | * | 12/1998 | Davila et al. ............... 264/103 |
| 5,853,400 A | * | 12/1998 | Samson ....................... 604/282 |

FOREIGN PATENT DOCUMENTS

| | | | | |
|---|---|---|---|---|
| EP | 344530 | * | 12/1989 | ................. 604/96 |
| EP | 0 597 506 A1 | | 5/1994 | |
| EP | 0 766 977 A1 | | 4/1997 | |
| EP | 0 850 655 A2 | | 7/1998 | |
| GB | 2016274 | | 9/1979 | |
| WO | WO 91/00118 | * | 1/1991 | ................. 604/96 |

OTHER PUBLICATIONS

Stamina Guiding Catheter brochure, Schneider (USA) Inc., 1992.

* cited by examiner

*Primary Examiner*—Sharon Kennedy
(74) *Attorney, Agent, or Firm*—Cook, Alex, McFarron, Manzo, Cummings & Mehler, Ltd.

(57) ABSTRACT

A balloon catheter is provided which has a long, atraumatic tip positioned distally of the balloon. The distal edge of the tip has an annular chamfer. The balloon catheter typically is of a variety having a relatively stiff distal end or balloon assembly, and the atraumatic tip enhances tracking of such balloons along a thinner guidewire.

29 Claims, 2 Drawing Sheets

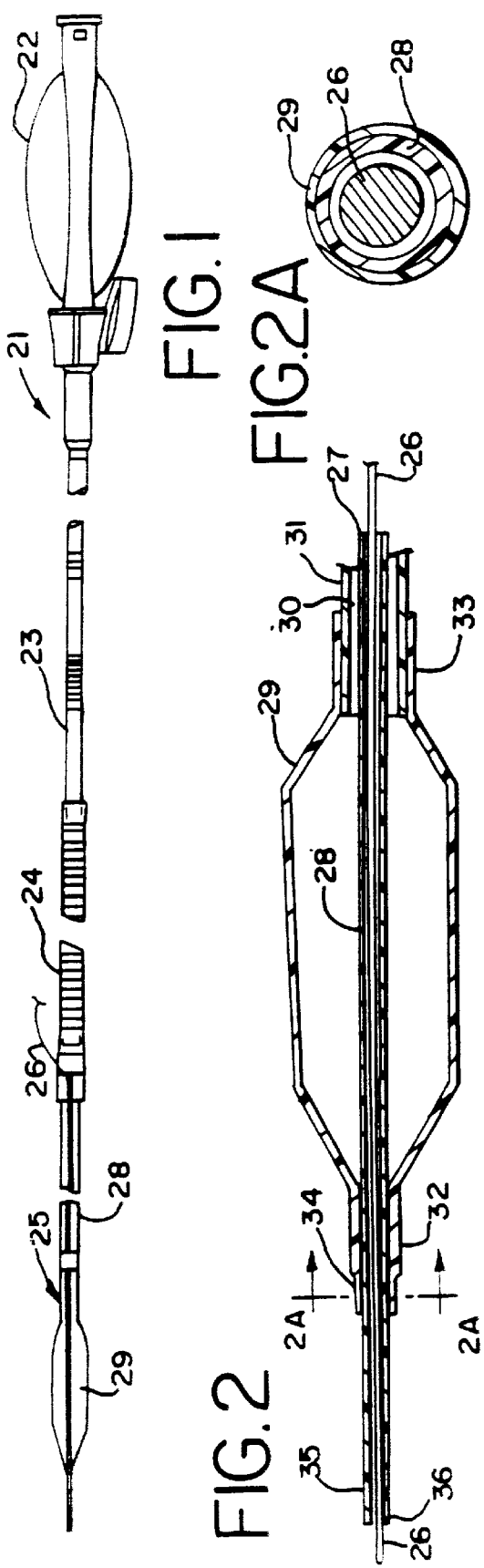
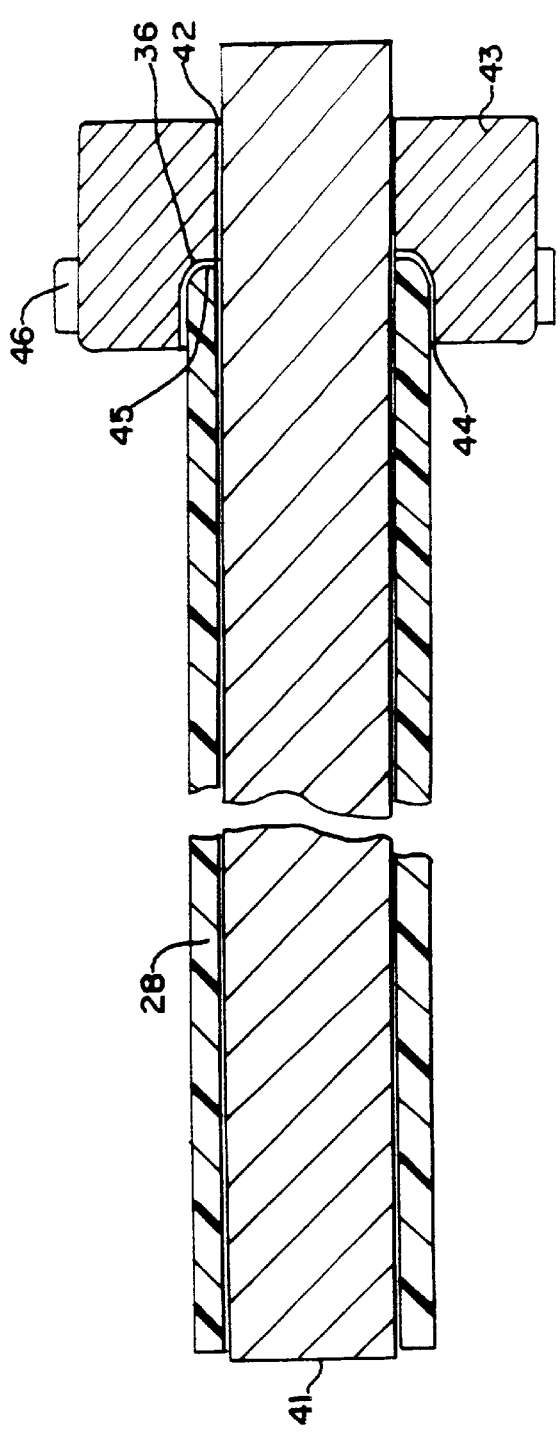

BALLOON CATHETER WITH ELONGATED FLEXIBLE TIP

DESCRIPTION

Background of the Invention

The present invention generally relates to a balloon catheter such as one for conducting dilatation procedures within the vascular system and in conjunction with a guidewire along which the balloon catheter is slidably moved for positioning and treatment. The balloon catheter incorporates an inner tube for receiving the guidewire therewithin. A distal portion of the inner tube has a securement location at which a distal leg of the balloon is secured to the inner tube. A relatively long tip of the catheter extends distally beyond this securement location. This tip has an external annular chamfer, which can be in combination with an internal annular taper. The result is improved tracking for situations and for guidewire and balloon catheter combinations which present tracking problems due to stiffer catheter distal portions, particularly when used with guidewires which allow for and provide curves of tighter radii within body vessels.

In certain balloon applications, components are included which increase the stiffness and generally reduce the bendability or flexibility at those distal portions of the balloon catheter which need to easily track an inserted guidewire along its tortuous path. Often, this tortuous path is provided by the thinner variety of guidewires, such as those used in coronary angioplasty or PTCA procedures. Stent delivery balloons and/or high burst pressure balloons are examples of these types of catheters having stiffer distal end portions. When a stent is positioned over a balloon, the overall stiffness of the distal end portion typically is increased considerably. Other examples of stiffer distal portions are those including a membrane, such as with the balloon, for delivery of pharmaceuticals or treatment materials. Catheters including coated balloons, radiation balloons, laser balloons, or ablation balloons are other examples where trackability is an especially difficult problem in many medical procedures. This situation generally occurs when the distal portion of the catheter embodies an approach which adds a component, and/or increases wall thicknesses and/or reduces material flexibility.

When it comes to tip lengths of balloon dilation catheters, there is a reluctance to extend the length of the distal tip. An elongated tip can impart a perception of a catheter which is too needle-like in appearance. There is also a concern that elongated tips have a tendency to kink when attempting to follow a relatively sharp bend or small radius curve of a flexible guidewire. Accordingly, in many applications, proposals for a longer tip have been met with concern and reluctance to attempt to prepare and use catheters having especially long tips.

At times, balloon catheters are called upon to perform functions in addition to dilatation of lesions and the like. For example, they can be used for delivering and implanting a stent, including applying radial pressure in order to "tack" an edge of the stent in place. These and other stents have a high pressure characteristic. Usually, such stent-delivery and/or high-pressure balloon catheters are somewhat stiffer and less flexible than balloon catheters intended for dilatation only. Other balloon catheters which are stiffer and/or less flexible than a typical dilatation catheter such as a percutaneous transluminal coronary angioplasty catheter include the following. Certain catheter designs include balloon membranes which are structured and positioned for delivering treatment pharmaceuticals or other medicaments and the like to specific locations within the body. Other balloon catheters include components, features, thicknesses or materials which bring about a reinforcing or additional feature which reduces pliability. These include catheters having coated balloons, radiation balloons, laser balloons, ablation balloons, and the like. Stiffer balloons along these lines also include balloons for dilatation of large coronary arteries, as well as balloons for primary dilatation of bypass grafts, and for treatment of saphenous veins, carotid peripheral vessels and other non-carotid peripheral vessels. Also in this category are dilatation catheters for neuroradiology. When used herein, these types of catheters are variously referred to as stiffer balloon catheters or balloon catheters having stiffer distal end portions.

These types of stiffer balloon catheters have been found to be associated with problems during delivery, especially when passing over guidewires along a curve or bend in the guidewire. Locations which are especially problematic in this regard include at bifurcation locations, along tortuous paths such as in the atrium, and other similar types of curved paths. If the catheter does not cleanly track over the guidewire, hang-ups tend to occur, resulting in prolapsing of the catheter, such as into the branch of the bifurcated vessel other than the one through which the catheter is passing. Accordingly, there is a need to address kinking difficulties of this type.

Another difficulty with balloon catheter tips involves attempting to maintain the tip to be as atraumatic as possible. In the past, heat sealing and/or attaching procedures have been used which in effect heat treat the entire tip or cause a stiffening at the attachment site. For example, for most materials, a heat treatment results in increased tip stiffness which necessarily detracts from the otherwise atraumatic nature of the material out of which the tip is made.

In accordance with the present invention, problems such as these are addressed through the use of a tip which includes as an important feature thereof a particularly long length. One would expect that a longer length tip would be stiffer because of its longer length (all other factors being equal). One would also expect that a longer tip would not track a guidewire as well as a shorter tip. One would also expect that a longer tip would not make a good radius curve when "cornering." Contrary to these expectations, the present invention enhances tracking and cornering and results in a tip having improved atraumatic properties when compared with other tips made of the same material.

SUMMARY OF THE INVENTION

In accordance with the present invention, a balloon catheter is provided which incorporates a longer and especially atraumatic tip. The distal end of the tip member or portion is spaced away from any balloon sealing location so as to avoid or least substantially minimize undesirable heat treatment. The distal edge of the long tip also has an annular chamfer which further enhances the atraumatic nature of the tip. The tip extends distally beyond the distalmost portion of the location at which the balloon is secured to the catheter shaft by a distance of at least about 0.140 inch (about 3.5 mm), and typically not more than about 0.300 inch (about 7.5 mm).

It is accordingly a general object of the present invention to provide an improved balloon catheter having a long and atraumatic tip.

Another object of this invention is to provide an improved balloon catheter which is of the stiffer balloon catheter variety and which tracks well over the guidewire.

Another object of the present invention is to provide an improved balloon catheter which has a stiffer distal end portion and has a long, atraumatic tip which "corners" well when passed over a guidewire, including a PTCA sized guidewire.

Another object of the present invention is to provide an improved balloon catheter which has enhanced path-finding action on the guidewire.

Another object of the present invention is to provide an improved balloon catheter having a tip with a flexibility tailored to the particular need of the catheter.

Another object of this invention is to provide an improved balloon catheter which provides a more gradual increase in distal segment stiffness so as to achieve better tracking of the guidewire through its curves and bends.

Another object of this invention is to provide an improved balloon catheter having a more atraumatic distalmost end.

Another object of the present invention is to provide an improved balloon catheter having a distal portion which provides better position retention should the guidewire be withdrawn too far in a proximal direction.

Another object of this invention is to provide an improved dilatation balloon catheter providing a gradual ramp or wedge structure at its distal end in order to better cross the long axis of a previously deployed stent or to cross through struts or wires of a previously deployed stent, especially when that stent is across a vessel side branch.

These and other objects, features and advantages of the present invention will be apparent from and clearly understood through a consideration of the following detailed description.

BRIEF DESCRIPTION OF THE DRAWINGS

In the course of this description, reference will be made to the attached drawings, wherein:

FIG. 1 is a generally elevational view of an example of a balloon catheter in accordance with the present invention;

FIG. 2 is an enlarged, longitudinal substantially cross-sectional view of the distal portion of a balloon catheter incorporating a long tip;

FIG. 2A is a cross-sectional view along the line 2A—2A of FIG. 2;

FIG. 3 is a cross-sectional view, partially broken away, illustrating a method and apparatus for chamfering of a long tip in forming the beveled edge according to the invention;

DESCRIPTION OF THE PREFERRED EMBODIMENTS

Figure 5:
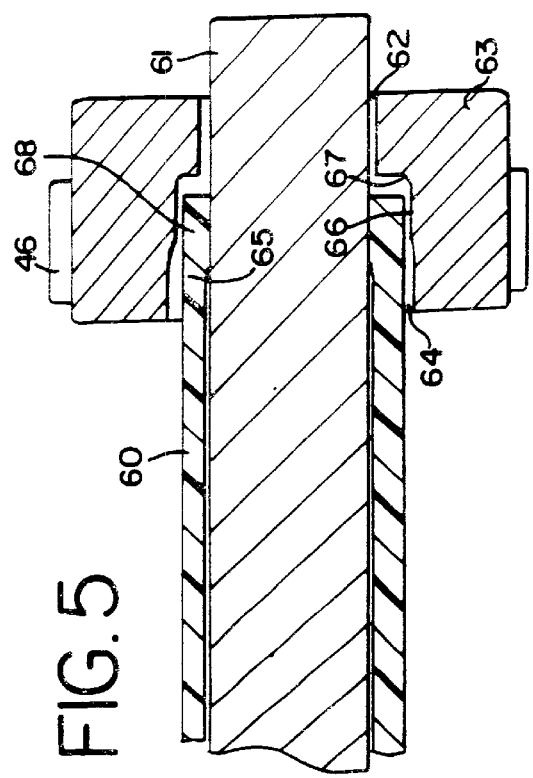
FIG. 5 is a view similar to FIG. 4, showing a subsequent step.
Figure 7:
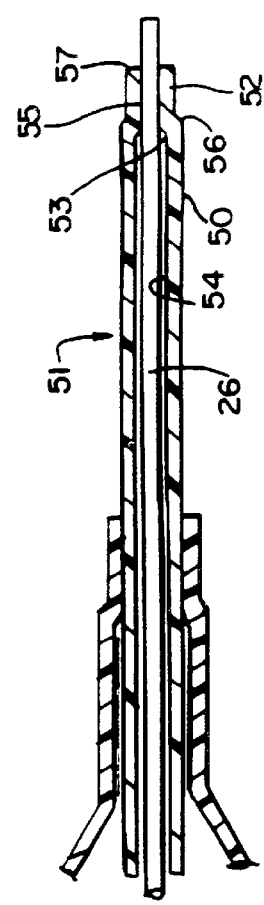
FIG. 7 is a longitudinal, generally cross-sectional view of a balloon catheter showing a tip as prepared in accordance with FIGS. 4, 5 and 6.

A dilatation catheter according to the invention is generally designated in FIG. 1 by reference numeral 21. It includes a hub assembly 22 of generally known structure for manipulating the catheter from a location outside of the body in a manner which is generally known in the art. An elongated catheter tube 23 is attached to the hub assembly by a suitable structure and approach. A transition assembly 24 can be provided distally thereof in order to provide a moderate-flexibility bridge between the elongated catheter 23 and a distal end assembly of the catheter, which is generally designated by reference numeral 25. A guidewire 26 is generally shown. It will be appreciated that the guidewire is in sliding engagement with the catheter. In the catheter which is illustrated, this sliding engagement is through the guidewire lumen 27 of an inner body tube 28. A balloon 29 is also shown.

The illustrated distal end assembly balloon member is made of a material suitable for a dilatation balloon, for example, and in accordance with an appropriate molding approach for that material. The balloon member 29 is securely attached to an outer body tube 31, which outer body tube is attached at its other end to the transition assembly 24 in this embodiment. The distal end assembly can incorporate a dual-lumen tube, for example, in order to provide the required guidewire lumen while also providing an inflation lumen 30 by which the balloon is inflated and deflated as needed during a procedure carried out with the catheter. The illustrated distal end assembly 25 is of a type having a so-called coaxial structure. This coaxial structure includes the outer body tube 31 and the inner body tube 28 which together define the inflation lumen 30 for the balloon 29. This type of coaxial structure is generally known. A distal leg portion 32 of the balloon is secured to a distal portion of the inner body tube, while a proximal leg portion 33 of the balloon is secured to the outer body tube 31.

Referring particularly to the securement of the distal leg portion 32 of the balloon to the inner body tube in this embodiment, a heat seal area 34 can be seen by which the distalmost portion of the leg is heat sealed onto a portion of the inner body tube which is spaced somewhat from the distalmost edge of an atraumatic tip 35. This spacing is sufficient such that any heat setting of the material of the atraumatic tip 35 is confined to a location that is spaced well away from the distal edge of the atraumatic tip. It is also possible to secure the legs of the balloon by the use of adhesives or other suitable procedures or means.

In the illustrated embodiments, the atraumatic tip 35 is a continuous extension of the inner body tube 28. It is also possible to have the tip be an initially separate component which is assembled onto the otherwise distal end portion of the catheter. Again, if this assembly takes an approach which would heat set the polymer out of which the tip is made, the length of the tip ensures that the distalmost portion of it is not heat set or otherwise detrimentally affected insofar as its flexibility is concerned.

It will be noted that the atraumatic tip includes a distal edge having an annular chamfer 36. This is better visible in FIG. 3, which depicts a method for the formation of this annular chamfer 36 of the atraumatic tip.

Referring more particularly to FIG. 3, an inner body tube 28 is shown positioned over a mandrel 41. In this embodiment, mandrel 41 has an outer diameter which closely fits within the inner diameter of the inner body tube 28, as well as within an opening 42 of an edge buff die 43. Edge buff die 43 also includes a larger generally cylindrical opening or countersink 44 which opens into and is coaxial with the cylindrical opening 42. It will be noted that the larger cylindrical opening includes a curved transition area 45 which is generally toroidal in configuration. This concave toroidal surface 45 corresponds to the shape of the annular chamfer 36 which is formed. A conventional heat source 46 is provided for imparting heat to the edge buff die 43, and especially to the concave toroidal surface 45 thereof. In the illustrated embodiment, the edge buff die 43 rotates along an axis common to the axis of the mandrel 41. Alternatively, the mandrel 41 and inner body tube 28 can rotate, while the edge buff die remains stationary or rotates as well.

With reference to the embodiment which is the subject of FIGS. 4, 5, 6 and 7, an approach similar to that in FIG. 3 is untaken, except as now described, in order to prepare an atraumatic tip 51 having a distal end 52 which has a slightly reduced inner diameter. The illustrated embodiment also shows a slightly reduced outer diameter. The result is a distal end 52 which more closely engages or "hugs" the guidewire 26 than does the rest of the atraumatic tip 51. More particularly, the distal end 52 is configured to have an inner annular ramp 53. Annular ramp 53 connects a cylindrical lumen 54 (which is at the diameter of the elongated atraumatic tip 50) and an inner cylindrical surface 55 of the distal end 52 (which has an internal diameter substantially equal to the outer diameter of the guidewire 26). By this approach, the entire circumference of the distal end of the atraumatic tip 51 engages the guidewire 26 when the inner cylindrical surface 55 slides along the outer surface of the guidewire.

Figure 4:
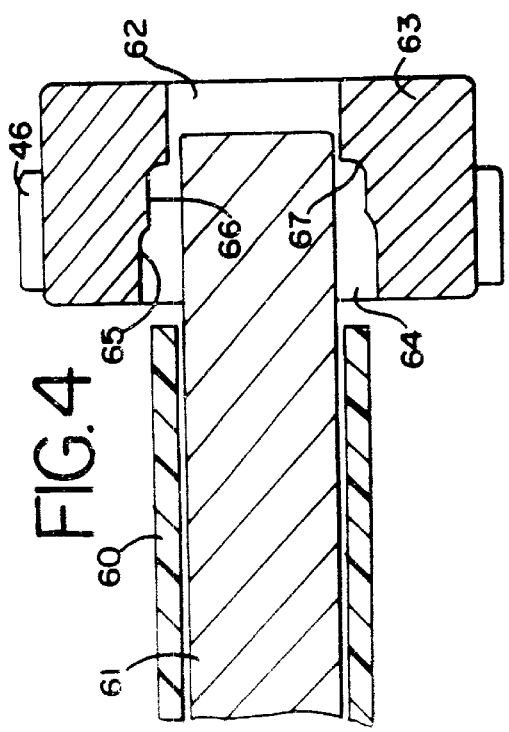
FIG. 4 is a substantially cross-sectional view illustrating an initial step in a method for forming a distal portion of an atraumatic tip according to the invention.
Figure 6:
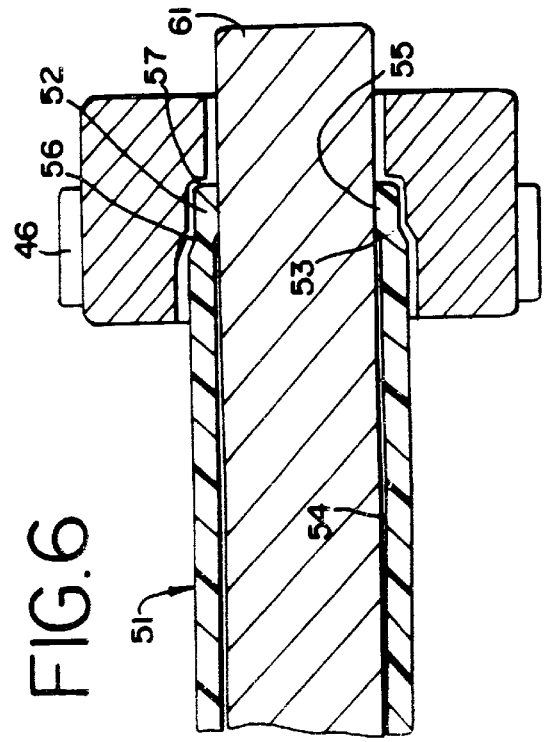
FIG. 6 is a view similar to FIG. 5 showing a further step.

Referring to FIGS. 4, 5 and 6, a method and equipment suitable for manufacturing the atraumatic tip 51 is illustrated. Tube 60 from which the atraumatic tip 51 is to be made is positioned over a mandrel 61, and the mandrel is fed into a cylindrical opening 62 through an edge buff die 63. A cylindrical opening 64, which is larger than the cylindrical opening 62, is provided at the entry side of the die 63 and is coaxial with the smaller cylindrical opening 62. Opening 64 includes an outer concave toroidal surface 65 which forms outer annular ramp 56 of the atraumatic tip. An intermediate cylindrical opening 66 is coaxial with the cylindrical opening 62. An inner concave toroidal surface 67 is provided for forming annular edge chamfer 57 of the long atraumatic tip 51.

In FIG. 5, it can be seen that the tube 60 and mandrel 61 are inserted into the edge buff die 63. This insertion is such that the leading end portion 68 of the tube 60 is force fit between the intermediate cylindrical opening 66 and the outer cylindrical surface of the mandrel 61. The force fit is a compression fit to the tip outer diameter. The cylindrical opening 62 is a slip fit mandrel support section. Rotation of the die and/or the mandrel with respect to each other, typically with the assistance of conventional heat source 46, causes the material of the leading end portion 68 of the tube 60 to re-form to the configuration generally shown in FIG. 6, which is the configuration of the distal end portion of the long atraumatic tip 51 shown in FIG. 7. The result of this procedure is the formation of an atraumatic tip 51 having an area of reduced lumen inner diameter, this area being at the distal end portion of the atraumatic tip.

Typically, the atraumatic tips in accordance with the invention are made of polymeric material which has been extruded into a cylindrical tube. In a preferred arrangement, the atraumatic tip is a coextrusion of two polymers, with the outer polymer being somewhat softer when within the body than is the inner polymer. An exemplary polymer suitable for the inner surface is polyethylene. The outer surface can be made of a nylon material or of a polyamide material, including homopolymers, copolymers and blends of homopolymers and copolymers. Nylon 12 materials are especially preferred. In making the distalmost portion of the atraumatic tip, at least the outer polymer should be susceptible to the type of heat buffing and heat shaping which is discussed herein. It will be appreciated that the heat buffing approach described does not heat treat the tip polymer material, so that the polymer will be soft and atraumatic when used within the human body. In a typical operation, the heat buffing is completed in about five seconds.

With the present invention, the distal segment or distal end assembly 25 of the catheter must traverse the tortuous path of the vasculature between the entry site and the final position in the vessel. The present invention is particularly useful in that the distal end assembly of stiffer balloon catheters has the ability to easily negotiate the tortuous path, which ability is otherwise compromised when using a stiffer balloon catheter which does not incorporate the longer atraumatic tip in accordance with the invention. These stiffer balloon catheters include high pressure balloons having a rated burst pressure of at least about 12 atmospheres, typically between 12 and 16 atmospheres.

The longer atraumatic tip of the balloon catheter 21 provides more tip material distal of the balloon seal. Avoiding heat treatment of the atraumatic tip, particularly at its distal end portion, enhances flexibility of the tip and controls the impact of processing on the atraumatic tip. The result is better tracking along the guidewire through curves and bends. The added length distal of the balloon also provides better position retention should the guidewire be withdrawn too far proximally during a procedure. The more gradual ramp or wedge at the distal end of the atraumatic tip provides for better crossing of the longitudinal axis of previous treatment sites, such as the location of a previously deployed stent. The long atraumatic tip provides improved pathfinding for stiffer balloon catheters while avoiding tip kinking or hang-ups, particularly along the thinner guidewires. A typical thinner diameter guidewire will have an outer diameter of 0.0014 inch (0.036 mm).

Important in tailoring the atraumatic tip to one having the desired properties includes a consideration of the modulus of the polymer material, tip wall thickness and guidewire size. These inputs are useful in determining the length, thickness, material Durometer hardness and column strength required for a particular long atraumatic tip. Generally speaking, the smaller the diameter of the guidewire, and the greater the stiffness of the balloon catheter distal end assembly, the longer the atraumatic tip should be. A usual minimum length for a long atraumatic tip is about 0.14 inch (about 3.5 mm). Generally speaking, the tip length will not exceed about 0.30 inch (about 7.5 mm). A typical longer atraumatic tip for a typical stiffer balloon catheter will have a length approximating 0.2 inch (approximately 5 mm). A general range is on the order about 4 mm to about 5 mm.

It will be understood that the embodiments of the present invention which have been described are illustrative of some of the applications of the principles of the present invention. Various modifications may be made by those skilled in the art without departing from the true spirit and scope of the invention.

What is claimed is:

1. A balloon catheter, comprising:

an elongated proximal shaft having an inflation lumen;

a distal portion extending distally beyond said elongated proximal shaft;

a balloon member on said distal portion, said balloon member having a generally cylindrical distal leg and access to said inflation lumen;

a guidewire lumen, said guidewire lumen being sized and shaped to slidably receive a guidewire therethrough, said guidewire lumen having a distal end portion, said balloon distal leg being secured to the distal portion at a location generally at the distal leg of the balloon member, such being a securement location;

a long flexible atraumatic tip of the catheter, said atraumatic tip being at the distalmost portion of the guidewire lumen, said tip extending distally beyond said securement location, said tip having a length of at least about 3.5 mm; and said tip has a distal edge having a buffed, soft non-heat treated annular chamfer, and at least a distal portion of said tip has a flexibility which is not negatively impacted by formation of said securement location.

2. The balloon catheter in accordance with claim 1, wherein said tip length is between about 3.5 mm and about 7.5 mm.

3. The balloon catheter in accordance with claim 1, wherein said tip length is between about 4 mm and about 5 mm.

4. The balloon catheter in accordance with claim 1, wherein said guidewire lumen is within an inner body tube through at least said distal portion of the catheter, and wherein said atraumatic tip is integral with said inner body tube.

5. The balloon catheter in accordance with claim 4, wherein said atraumatic tip and said inner body tube are constructed of the same length of tubing.

6. The balloon catheter in accordancre with claim 1, wherein said long atraumatic tip has a selected length thereof having a reduced internal diameter which corresponds to the external diameter of a guidewire to be received through the guidewire lumen, said reduced internal diameter being less than that of the remainder of the guidewire lumen.

7. The balloon catheter in accordance with claim 6, wherein said reduced internal diameter extends to the distalmost edge of the tip at which said annular chamfer is positioned.

8. The balloon catheter in accordance with claim 7, wherein said atraumatic tip has two internal diameters, one such internal diameter generally corresponding to that of the guidewire lumen, and the other such internal diameter being said reduced internal diameter.

9. The balloon catheter in accordance with claim 7, wherein said atraumatic tip has at least two sections having different outer diameters, with the smaller of said different outer diameters being at the distal portion of the tip, and wherein an outer annular ramp is positioned between the two sections of the tip.

10. The balloon catheter in accordance with claim 1, wherein said annular chamfer at the distal edge of the atraumatic tip has been made by a process including rotational buffing of the distal edge of a tube so as to form said annular chamfer.

11. A balloon catheter and guidewire combination, comprising:

an elongated proximal shaft having an inflation lumen;

a distal portion extending distally beyond said elongated proximal shaft;

a balloon member on said distal portion, said balloon member having a generally cylindrical distal leg and access to said inflation lumen;

a guidewire lumen, said guidewire lumen being sized and shaped to slidably receive a guidewire therethrough, said guidewire lumen having a distal end portion, said balloon distal leg being secured to the distal portion at a location generally at the distal leg of the balloon member, such being a securement location;

a long flexible atraumatic tip of the catheter, said atraumatic tip being at the distalmost portion of the guidewire lumen, said tip extending distally beyond said securement location, said tip having a length of at least about 3.5 mm;

said tip has a distal edge having a buffed, soft non-heat treated annular chamfer, and at least a distal portion of said tip has a flexibility which is not negatively impacted by formation of said securement location; and an elongated guidewire slidably positioned within said guidewire lumen.

12. The combination in accordance with claim 11, wherein said tip length is between about 3.5 mm and about 7.5 mm.

13. The combination in accordance with claim 11, wherein said guidewire lumen is within an inner body tube through at least said distal portion of the catheter, and wherein said atraumatic tip is integral with said inner body tube.

14. The combination in accordance with claim 11, wherein said long atraumatic tip has a selected length thereof having a reduced internal diameter which corresponds to the external diameter of a guidewire to be received through the guidewire lumen, said reduced internal diameter being less than that of the remainder of the guidewire lumen.

15. The combination in accordance with claim 14, wherein said selected length of reduced internal diameter extends to the distalmost edge of the tip at which said annular chamfer is positioned and wherein said atraumatic tip has two internal diameters, one such internal diameter generally corresponding to that of the guidewire lumen, and the other such internal diameter being said reduced internal diameter.

16. The combination in accordance with claim 14, wherein said atraumatic tip has at least two sections having different outer diameters, with the smaller of said different outer diameters being at the distal portion of the tip, and wherein an outer annular ramp is positioned between the two sections of the tip.

17. The combination in accordance with claim 16, wherein said annular chamfer at the distal edge of the atraumatic tip has been made by a process including rotational buffing of the distal edge of a tube so as to form said annular chamfer.

18. The balloon catheter in accordance with claim 1, wherein said atraumatic tip comprises a coextrusion of at least two polymers, the outer polymer being somewhat softer when within the body than the inner polymer.

19. The balloon catheter in accordance with claim 21, wherein the outer polymer includes a nylon, a polyamide or a combination thereof and the inner polymer is polyethylene.

20. The combination catheter in accordance with claim 11, wherein said atraumatic tip comprises a coextrusion of at least two polymers, the outer polymer being somewhat softer when within the body than the inner polymer.

21. The combination catheter in accordance with claim 23, wherein the outer polymer includes a nylon, a polyamide or a combination thereof and the inner polymer is polyethylene.

22. The balloon catheter in accordance with claim 1, wherein said atraumatic tip comprises a coextrusion of at least two polymers, one of said polymers being somewhat softer when within the body than the other said polymer.

23. The balloon catheter in accordance with claim 1 where in said atraumatic tip has at least two sections having different outer diameters, with the smaller of said different outer diameters being at the distal portion of the tip, and wherein an outer annular ramp is positioned between the two sections of the tip.

24. The combination in accordance with claim 11, wherein said atraumatic tip comprises a coextrusion of at least two polymers, one of said polymers being somewhat softer when within the body than the other said polymer.

25. The combination in accordance with claim 11, wherein said atraumatic tip has at least two sections having different outer diameters, with the smaller of said different outer diameters being at the distal portion of the tip, and wherein an outer annular ramp is positioned between the two sections of the tip.

26. A balloon catheter, comprising:

an elongated proximal shaft having an inflation lumen;

a distal portion extending distally beyond said elongated proximal shaft;

a balloon member on said distal portion, said balloon member having a generally cylindrical distal leg and access to said inflation lumen;

a guidewire lumen, said guidewire lumen being sized and shaped to slidably receive a guidewire therethrough, said guidewire lumen having a distal end portion, said balloon distal leg being secured to the distal portion at a location generally at the distal leg of the balloon member, such being a securement location;

a flexible atraumatic tip of the catheter, said atraumatic tip being at the distalmost portion of the guidewire lumen, said tip extending distally beyond said securement location; and said tip has a distal edge having a buffed, soft non-heat treated annular chamfer, and at least a distal portion of said tip has a flexibility which is not negatively impacted by formation of said securement location, and said tip comprises a coextrusion of at least two polymers, one of said polymers being somewhat softer when within the body than the other said polymer.

27. The balloon catheter of claim 26, wherein of said two polymers, the outer polymer is softer than the inner polymer.

28. A balloon catheter and guidewire combination, comprising:

an elongated proximal shaft having an inflation lumen;

a distal portion extending distally beyond said elongated proximal shaft;

a balloon member on said distal portion, said balloon member having a generally cylindrical distal leg and access to said inflation lumen;

a guidewire lumen, said guidewire lumen being sized and shaped to slidably receive a guidewire therethrough, said guidewire lumen having a distal end portion, said balloon distal leg being secured to the distal portion at a location generally at the distal leg of the balloon member, such being a securement location;

a flexible atraumatic tip of the catheter, said atraumatic tip being at the distalmost portion of the guidewire lumen, said tip extending distally beyond said securement location;

said tip has a distal edge having a buffed, soft non-heat treated annular chamfer, and at least a distal portion of said tip has a flexibility which is not negatively impacted by formation of said securement location and comprises a coextrusion of at least two polymers, one of said polymers being somewhat softer when within the body than the other said polymer; and an elongated guidewire slidably positioned within said guidewire lumen.

29. The combination of claim 28, wherein of said two polymers, the outer polymer is softer than the inner polymer.

* * * * *

UNITED STATES PATENT AND TRADEMARK OFFICE
CERTIFICATE OF CORRECTION

PATENT NO. : 6,402,720 B1
DATED : June 11, 2002
INVENTOR(S) : Miller et al.

It is certified that error appears in the above-identified patent and that said Letters Patent is hereby corrected as shown below:

Column 4,
Line 53, after "This is" insert -- perhaps --.

Column 7,
Line 26, delete "accordancre" and insert -- accordance --.

Column 8,
Line 46, delete "claim 21" and insert -- claim 18 --.
Line 48, after "thereof" insert -- , --.
Line 50, delete "catheter".
Line 54, delete "catheter".
Line 55, delete "23" and insert -- 20 --.
Line 56, after "thereof" insert -- , --.
Lines 62-63, delete "where in" and insert -- wherein --.

Signed and Sealed this

Fifth Day of November, 2002

Attest:

JAMES E. ROGAN
Attesting Officer
Director of the United States Patent and Trademark Office